United States Patent [19]

Fowler et al.

[11] 4,167,521

[45] Sep. 11, 1979

[54] RECOVERY OF NITRATED COMPOUNDS USING SOLVENT EXTRACTION AND DISTILLATION

[75] Inventors: Frank C. Fowler, Kansas City, Mo.; Don H. Smith, Dallas, Tex.

[73] Assignee: Atlas Powder Company, Dallas, Tex.

[21] Appl. No.: 899,261

[22] Filed: Apr. 24, 1978

[51] Int. Cl.$^2$ .......................... C07C 77/02; B01D 3/10
[52] U.S. Cl. ..................................... 260/467; 203/11; 203/91; 260/705
[58] Field of Search .................... 203/11, 91; 260/467, 260/705

[56] References Cited

U.S. PATENT DOCUMENTS

| 262,913 | 8/1882 | Armandy | 203/91 |
|---|---|---|---|
| 3,620,928 | 11/1971 | Miserlis | 203/91 |
| 3,721,610 | 3/1973 | Chaintron | 203/91 |

FOREIGN PATENT DOCUMENTS

| 734501 | 5/1966 | Canada | 260/467 |
|---|---|---|---|
| 788946 | 1/1958 | United Kingdom | 260/467 |

OTHER PUBLICATIONS

Urbanski, Chemistry and Technology of Explosives, vol. II, Pergamon Press, New York, 1965, pp. 37, 82, 83 and 142 to 145.

*Primary Examiner*—Leland A. Sebastian
*Attorney, Agent, or Firm*—Richards, Harris & Medlock

[57] ABSTRACT

A method for separating an aqueous solution which contains minor amounts of nitrated esters which are only slightly soluble in water is provided. Separation of the nitrated esters, which include ethylene glycol dinitrate and nitroglycerin, is effected by contacting the aqueous solution with an organic phase of ethylene glycol dinitrate for a period of time sufficient to allow extraction of the nitroglycerin in solution into the ethylene glycol dinitrate phase. The organic ethylene glycol dinitrate phase is then separated from the aqueous solution, and the latter is distilled at a temperature of from about 50 degrees F. to about 200 degrees F. at a lower than atmospheric pressure. Upon completion of the separation process water, which is substantially free of nitrated esters, is suitable for discharge and return to a natural environment.

12 Claims, 2 Drawing Figures

RECOVERY OF NITRATED COMPOUNDS USING SOLVENT EXTRACTION AND DISTILLATION

BACKGROUND OF THE INVENTION

This invention relates to the recovery of nitrated esters from water. In another aspect this invention relates to purification of the wash or process water of explosive manufacturing processes where it is desirable to recover substantially all of the nitrated esters contained in the water prior to its release. Still another aspect of this invention relates to the separation of an aqueous solution which contains minor amounts of nitrated esters of polyalcohols which are only slightly soluble in water. Further, this invention relates to the extraction of dissolved portions of nitroglycerin from an aqueous solution by contacting said solution with ethylene glycol dinitrate.

The commercial production of glycerol nitrate (also known as nitroglycerin) and ethylene glycol dinitrate, for example, for explosive compositions normally involves operations including nitration, separation of spent nitric acids and purification by neutralization and washing. During the purification and washing steps, large volumes of water are used which come into contact with the nitrated esters. Because the solubility of these nitrated esters in water is very low, the water and a major portion of the nitrated esters can be separated easily. However, a limited quantity of the nitrated esters is dissolved in the wash or process water and heretofore has been discharged with the water phase. Presently, the water effluents only contain the amounts of nitrated esters which can be dissolved in the water. That is, for reasons of safety, the effluent water contains amounts of nitrated esters which do not exceed the saturation point of the water at the temperature at which it is discharged. Recently, however, the Environmental Protection Agency has proposed more stringent effluent limitations and guidelines regarding the maximum COD (chemical oxygen demand) and BOD (biological oxygen demand) which effluents from explosive manufacturing plants may have. See E.P.A. Proposed Regulation, Section 457.10–457.12, 41 Fed. Reg. 10184 (1976). Because COD requirements are directly related to the concentration of the nitrated esters in the effluent water, a process for the removal of nitrated esters which have become dissolved in the water is desirable.

Recently, it has been discovered that aqueous solutions containing dissolved nitrated esters of polyalcohols such as nitroglycerin, ethylene glycol dinitrate, 1,2-propylene glycol dinitrate, and 1,3-propylene glycol dinitrate, for example, which are all characterized as being only slightly soluble in water, can be separated by distilling the aqueous solution at temperatures in the range of from about 50 degrees to about 200 degrees F. under pressures of from about 10 to about 500 mm of mercury. This process is set forth in detail in applicant's co-pending application entitled "RECOVERY OF NITRATED COMPOUNDS FROM WATER", Ser. No. 721,773, filed Sept. 9, 1976, now U.S. Pat. No. 4,066,514, which is hereby incorporated by reference. This process provides a very effective means for separating a major portion of the dissolved nitrated esters found in waste water of explosive manufacturing plants. While both nitroglycerine and ethylene glycol dinitrate, for example, can be separated from waste waters in this manner the above described process is much more effective in the separation of ethylene glycol dinitrate than for nitroglycerine. Therefore, a process whereby the nitroglycerine contents of wash and process waters of explosive plants can be reduced below the levels obtainable with the above-described distillation process is desirable.

SUMMARY OF THE INVENTION

The present invention provides a process whereby the dissolved portion of nitrated esters which are only slightly soluble in water can be effectively separated from the water, thereby lowering the COD requirements of the water and rendering it suitable for discharge to a natural environment. It has been discovered that the nitroglycerin content of aqueous solutions containing minor amounts thereof can be significantly lowered by contacting the aqueous solution with an organic phase of ethylene glycol dinitrate which acts as a solvent to extract a substantial portion of the nitroglycerin dissolved in the aqueous solution. Therefore, the nitroglycerin content of the aqueous solutions of nitrated esters which comprise the feed stream for the aforementioned type of distillation process can be lowered significantly by employing ethylene glycol dinitrate as an extraction solvent. By pretreating the waste water with such an extraction process the distillation process, which is very effective for removal of ethylene glycol dinitrate, can be employed to lower the content of those nitrated esters in the aqueous solutions to about 200 ppm nitroglycerin, and about 20 ppm ethylene glycol dinitrate.

DETAILED DESCRIPTION OF THE INVENTION

Nitrated esters which are produced for use in explosive compositions include, for example, nitroglycerin, ethylene glycol dinitrate, and propylene glycol dinitrate. Generally, the solubility of these nitrated esters in water is characteristically low. For example, the solubility of nitroglycerin in distilled water at 20 degrees C. is 0.138 g/100 g water. The solubility of ethylene glycol dinitrate is 0.68 g/100 g of distilled water at 20 degrees C. Accordingly, separation of the nitrated esters from the water used in explosive manufacturing processes has been heretofore accomplished by allowing the water to separate from the organic liquids in settling tanks and simply withdrawing the water from the top of the settling tank and the nitrated esters from the bottom of the tank. However, some of the nitrated esters do form a true solution with the water and cannot be separated in this manner. The term "slightly soluble" as herein employed refers to nitrated esters which, under normal atmospheric pressure and ambient temperatures, such as about 25 degrees C., will dissolve in water in a quantity of no more than about 1 weight percent of the total solution, which corresponds to about 10,000 ppm.

It has been discovered that by contacting the aqueous solution containing minor dissolved amounts of nitroglycerin with an organic phase of ethylene glycol dinitrate, substantial portions of the nitroglycerin will be extracted from the aqueous solution and into the ethylene glycol dinitrate solvent. Thus, by allowing the organic phase of ethylene glycol dinitrate to contact the aqueous solution containing minor amounts of nitroglycerin for a period of time sufficient to allow solvent extraction to occur, and subsequently separating the organic phase of ethylene glycol dinitrate solvent (containing minor portions of extracted nitroglycerin) from the aqueous solution, substantial portions of the nitroglycerin can be separated from the aqueous solution. Up to about 75% of the nitroglycerin present in the waste water can be removed in this manner, depending upon the economics involved in achieving maximum mass transfer efficiency.

Generally, a volume-to-volume ratio of from about 1:500 to about 1:20 ethylene glycol dinitrate to nitroglycerin aqueous solution can be employed to effect the extraction. Of course, these volume ratios will vary according to contact times and the type of extraction process employed.

The aqueous solution from which the nitroglycerin has been extracted may contain various other dissolved nitrated esters of polyalcohols such as 1,2-propylene glycol dinitrate, and 1,3-propylene glycol dinitrate, as well as ethylene glycol dinitrate. Since ethylene glycol dinitrate is slightly soluble in water, contacting the aqueous solution with a solvent phase thereof may cause an increase in the ethylene glycol dinitrate concentration of the aqueous solution. Therefore, the aqueous solution, once separated from the ethylene glycol dinitrate solvent, can, in one embodiment of the present invention, be passed to a distillation column wherein the ethylene glycol dinitrate and other nitrated esters of polyalcohols are separated from the aqueous solution by distillation at temperatures in the range of from about 50 degrees F. to about 200 degrees F. and preferably in the range of from about 100 degrees F. to about 150 degrees F. Pressure during such distillation is adjusted to maintain a temperature within these ranges and can vary from about 10 to about 500 mm of mercury. By combining the extraction and distillation processes in this manner the concentration of nitrated esters of polyalcohols in the process and wash waters of explosive manufacturing plants can be reduced to levels acceptable for return of the waters to a natural environment without detrimental environmental effect.

Extraction of nitroglycerin from the aqueous solution can be effected by any number of conventional extraction techniques including co-current and counter-current extraction procedures, for example. The extraction can be accomplished by allowing the ethylene glycol dinitrate solvent to contact a continuous phase of the aqueous solution, or can be effected by passing a dispersed aqueous solution phase through a continuous phase of ethylene glycol dinitrate. Thus, in one embodiment of the present invention the aqueous solution containing nitroglycerin can be introduced at the bottom of a holding tank of ethylene glycol dinitrate and allowed to rise therethrough to effect the extraction of nitroglycerin into the solvent phase. Alternatively, the ethylene glycol dinitrate can be fed to the top of a column of the aqueous solution of nitrated esters and allowed to contact the aqueous solution as it moves, by gravitational force, through the aqueous solution.

The following is a general description of several different types of extraction processes which may be employed within the scope of the subject invention to remove nitroglycerin from aqueous solutions thereof by employing ethylene glycol dinitrate as a solvent therefor in a liquid liquid extraction type process. The term "extract" as used hereinbelow refers to the ethylene glycol dinitrate solvent containing minor amounts of extracted nitroglycerin and the term "raffinate" refers to the aqueous solution of the nitrated esters which has been contacted with the solvent to remove substantial portions of the nitroglycerin contained therein. Thus, the most simple liquid liquid extraction process comprises contacting the ethylene glycol dinitrate solvent with the amount of aqueous solution of nitrated esters (containing nitroglycerin) which is to be extracted. Simple multi-stage contact wherein the total quantity of ethylene glycol dinitrate solvent to be used is divided into separate portions and the aqueous feed is then treated with each of the portions of fresh solvent in a series of separate steps or stages, raffinate from the first extraction step being treated with fresh solvent in a second stage, and so on, can also be employed. Countercurrent multi-stage contact is an alternative method and comprises the step of introducing fresh solvent and feed at opposite ends of a series of extraction stages. Thus the extract and raffinate layers pass continuously and countercurrent from stage to stage through the system. Any number of stages may be employed, the more common numbers being 2 to 8. Continuous countercurrent contact can be employed wherein one of the phases is subdivided and allowed to pass continuously and counter-currently through the other phase, which is not dispersed. Either the ethylene glycol dinitrate solvent or the aqueous solution of nitrated esters may be subdivided and allowed to pass through the other. This could be accomplished either in a packed column or an unpacked spray tower, for example. Any of the above described methods and others well known to those in the art of extraction processes can be employed within the scope of the subject invention to remove nitroglycerin contained in process or wash waters from explosive manufacturing plants by using ethylene glycol dinitrate as a solvent.

Figures 1, 2:
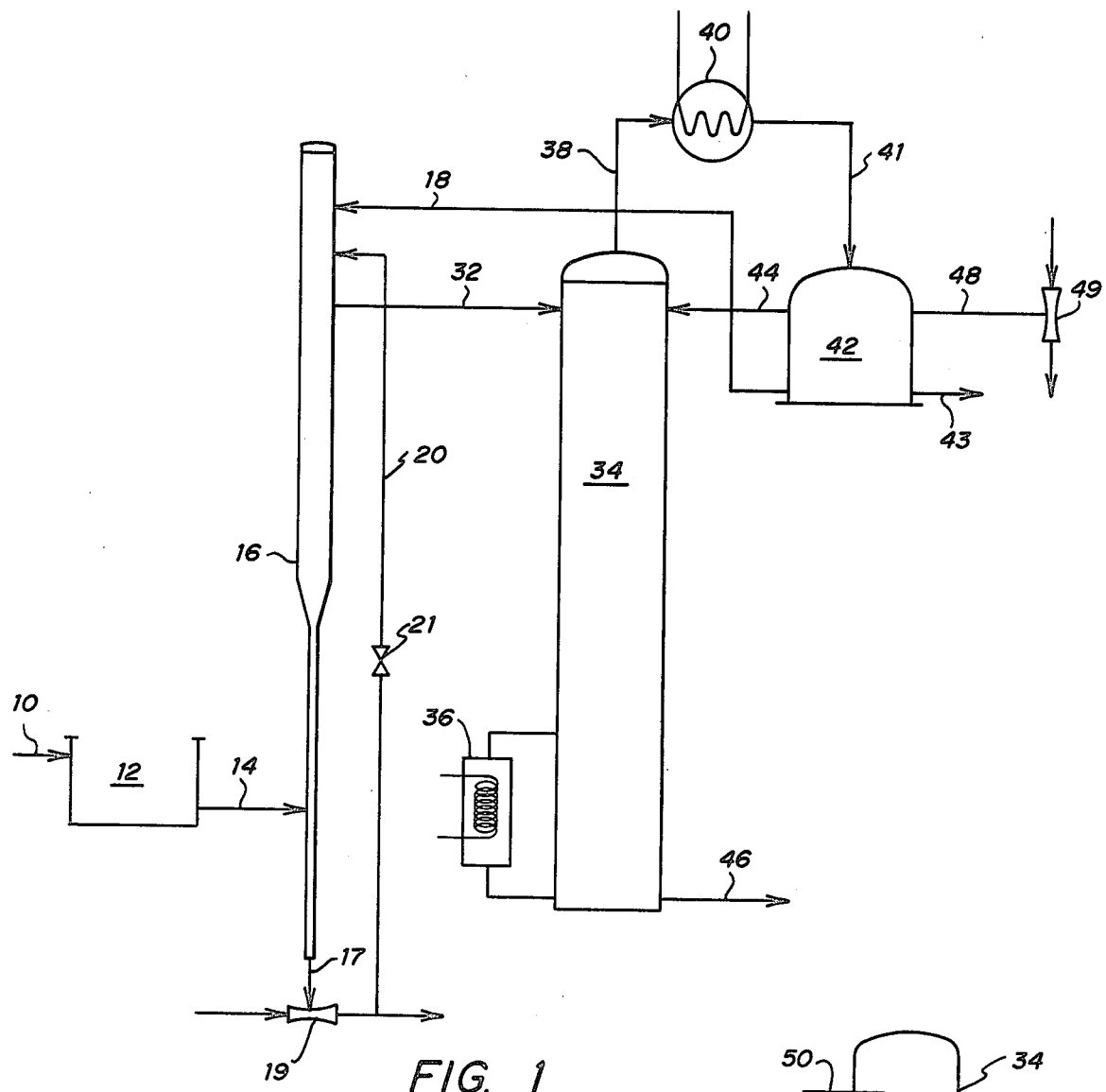
FIG. 1 depicts a schematic representation of one embodiment of the invention.
FIG. 2 depicts a schematic representation of a second embodiment of the invention.

The method of the present invention will hereinafter be described in detail with reference to FIG. 1 as applied to a process for separation of nitrated esters from wash or process waters from an explosive manufacturing process. It is to be understood that the broad scope of this invention is not to be limited to the described embodiments herein.

Generally, the manufacture of explosives includes the nitration of various compounds in conventional types of nitration equipment. The effluent from such nitration includes a mixture of acids, nitrated compounds and water. Water may be added, in some cases, at various stages of the manufacturing process and said water is herein referred to as "process water". The effluent from the nitrators is normally passed into neutralizing units where it is contacted with sodium carbonate or other alkali chemicals to neutralize the acids present therein. Water containing such neutralizing chemicals is hereinafter referred to as "wash water". After said neutralization or washing procedures the mixture of water and nitrated compounds is fed to a settling tank or series of settling tanks where the organic phase of the mixture separates from the water phase. Once the organic phase has been separated and recovered the wash and/or process water can be passed by a conduit 10 to a holding tank 12, as depicted in FIG. 1 where it is allowed to reach ambient temperatures. The wash or process water reaching holding tank 12 contains substantially no undissolved amounts of nitrated esters and is, in fact, an aqueous solution of the nitrated esters containing less than about 1 weight percent (10,000 ppm) of said nitrated esters. The aqueous solution containing the nitrated esters is then fed by a conduit 14 to any of a number of types of conventional extraction columns such as column 16. The wash or process water flows upward through extraction column 16 at flow rates of about 15 gallons per minute, for example, and is contacted therein by the ethylene glycol dinitrate solvent phase. As depicted in the drawing, the ethylene glycol dinitrate can be fed, near the top of the extraction column, by a conduit 18 leading from distillate collection tank 42 described in detail below. Flow rates of from about 0.05 to about 1.0 gallons per minute of the solvent phase can be employed, for example, with the above exemplary flow rates of the aqueous solution containing nitroglycerin. The ethylene glycol dinitrate phase containing the extracted nitroglycerin can be removed from the bottom of extraction column 16 via outlet conduit 17 with the aid of a vacuum source, such as aspirator 19. Conduit 20 allows part of the ethylene glycol dinitrate phase to be recycled to the top of the extraction column 16 by opening control valve 21. The aqueous solution, having had substantial amounts of the nitroglycerin dissolved therein extracted therefrom, is then passed via conduit 32 into distillation column 34 near the top of the column. The distillation column can include conventional types of packing which are well known in the industry. In addition, empty columns or columns having sieve plates, which do not allow dangerous amounts of the explosive nitrated esters to be retained thereon, can be employed. The bottom of distillation column 34 is equipped with reboiler 36 heated by a medium such as water, or steam, for example, where the maximum temperature can be kept below about 200 degrees F. The boil-off rate is adjusted so that about 5 to about 80% of the feed is vaporized. For example, when a mixture of ethylene glycol dinitrate and nitroglycerin is being separated and the ethylene glycol dinitrate comprises a major portion of the nitrated esters, a boil-off rate of from about 5% to about 30% can be employed. The vapor containing nitrated esters and water is drawn off the top of the column by a conduit 38 and is passed through a conventional condensing unit 40 and conduit 41 and is collected in distillate collection tank 42. The water phase of the condensed distillate will separate from the nitrated ester phase of the distillate and can be returned to the top of distillation column 34 by conduit 44 if desired. The condensed nitrated ester phase of the distillate, which is rich in ethylene glycol dinitrate, may be drawn off the bottom of distillate collection tank 42 via conduit 18 and fed to the extraction column as described above. Excess condensed nitrated esters can be removed via conduit 43. Water, which is substantially free of any nitrated esters can be withdrawn as bottom product from the distillation column 34 via conduit 46. Water processed in this manner can have the content of nitrated esters lowered below 220 ppm. More specifically the ethylene glycol dinitrate content of water processed in this matter can be lowered to about 20 ppm and the nitroglycerin content to about 200 ppm. A vacuum source 49 sufficient to allow operation of the distillation column at pressures from about 10 mm of mercury to about 500 mm of mercury is connected to this system by a vacuum line 48 which leads to distillate collection tank 42.

Now referring to FIG. 2, a second embodiment of the process of the subject invention will be described. In addition to the apparatus described above, the process of the subject invention can also be carried out conveniently utilizing a separator located at the top of the column directly under a condensing unit. Thus, condenser 50 provides for condensation of the vapor phase represented by arrows 52 rising through the annular vapor column portion 54 of the separator and around top plate 56 thereof. Upon condensation, the vapor phase drops back onto top plate 56 and the surrounding separator plate 58 further described hereinbelow. The condensate will separate into a water phase 60 floating on top of an organic phase 62 which normally will consist essentially of ethylene glycol dinitrate. Reflux tube 64 provides for the return of the water phase to the distillation column. The ethylene glycol dinitrate organic phase 62 leaves the distillation column 34 via feed inlet 66. Separator plate 58 collects the organic phase 62 which flows downward into feed conduit 66, for example by providing sloped surface 58a which communicates with feed conduit 66. Feed conduit 66 slopes downward and away from distillation column 34 and into an extraction column 16 substantially as shown in FIG. 1. Also as shown in FIG. 1, a feed conduit 14 delivers the aqueous solution of nitrated esters to the bottom of an extraction column 16 and the aqueous feed travels upward through extraction column 16 passing countercurrent to the organic phase 62 which is delivered to the top of extraction column 16 via feed conduit 66. Thus, the aqueous solution of nitrated esters enters distillation column 34 via feed conduit 66, and flows, along with some condensed water vapors, into distillation column 34 via reflux tube 64. It is, of course, important to adjust operating conditions such that the ethylene glycol dinitrate phase (which may be in the form of droplets at this point) does not rise above the level of reflux tube 64. The organic phase 62 travels out of the distillation column via feed conduit 66, through extraction column 16 and countercurrent to the aqueous solution, and may be withdrawn at the bottom of extraction column 16 by applying a vacuum source such as aspirator 19 (see FIG. 1).

While this invention has been explained in relation to its preferred embodiment, it is to be understood that various modifications thereof will now become apparent to those skilled in the art upon reading the specification and it is intended to cover such modifications as fall within the scope of the appended claims.

I claim:

1. A process for separating nitroglycerin from an aqueous solution thereof comprising:

contacting said aqueous solution of nitroglycerin with an effective amount of ethylene glycol dinitrate to thereby extract said nitroglycerin out of said aqueous solution and into said ethylene glycol dinitrate and thereafter separating the resulting ethylene glycol dinitrate phase from the resulting aqueous solution.

2. The process of claim 1 wherein the volumetric ratio of ethylene glycol dinitrate phase to aqueous solution of nitroglycerin is in the range of from about 1:500 to about 1:20.

3. In a process for removing nitroglycerin from an aqueous solution containing minor amounts thereof, the improvement comprising:

contacting said aqueous solution with ethylene glycol dinitrate in volumetric ratios of ethylene glycol dinitrate to aqueous solution of from about 1:500 to about 1:20 for a period of time sufficient to allow extraction of at least a portion of said nitroglycerin out of said aqueous solution and into said ethylene glycol nitrate to occur, and thereafter separating the resulting ethylene glycol dinitrate phase from the resulting aqueous solution.

4. A process for separating ethylene glycol dinitrate and nitroglycerin from an aqueous solution thereof comprising:
   (a) contacting said aqueous solution with a solvent comprising ethylene glycol dinitrate for a period of time sufficient to allow extraction of at least a portion of said nitroglycerin into said ethylene glycol dinitrate phase to occur;
   (b) separating the resulting aqueous solution from the resulting ethylene glycol dinitrate phase; and
   (c) distilling the resulting aqueous solution from which at least a portion of said nitroglycerin has been extracted at a temperature of from about 50 degrees F. to about 200 degrees F. and at less than atmospheric pressures to thereby separate ethylene glycol dinitrate from the resulting aqueous solution.

5. A method for separating nitrated esters from a water solution which contains less than about 1 weight percent of nitrated esters of polyalcohols including ethylene glycol dinitrate and nitroglycerin comprising:
   (a) contacting said water solution with a solvent comprising ethylene glycol dinitrate in a volumetric ratio of from about 1:500 to about 1:20 ethylene glycol dinitrate to water solution to thereby extract nitroglycerin from said water solution and into said solvent;
   (b) separating the resulting ethylene glycol dinitrate phase from the resulting water solution;
   (c) passing the resulting water solution into a distillation zone and heating said water to a temperature of from about 50 degrees F. to about 200 degrees F. at a lower than atmospheric pressure in the range of from about 10 to about 500 millimeters of mercury;
   (d) withdrawing a vapor stream comprising said nitrated esters and water from the top of said distillation zone;
   (e) cooling said vapor stream in a cooling zone to condense said water and said nitrated esters to form a water phase and nitrated ester phase;
   (f) separating the resulting condensed water phase from the resulting nitrated ester phase;
   (g) withdrawing the bottom product of said distillation zone which comprises water which is substantially free of said nitrated esters.

6. The method of claim 5 wherein the nitrated ester phase separated from said vapor stream is comprised substantially of ethylene glycol dinitrate and at least a portion of said ethylene glycol dinitrate is employed to extract nitroglycerin from said water solution.

7. A process for separating mixtures of nitrated esters comprising ethylene glycol dinitrate and nitroglycerin from a water solution containing less than about 1 weight percent thereof comprising:
   (a) passing said water solution through an extraction zone in contact with an organic phase of ethylene glycol dinitrate to thereby extract nitroglycerin from said water solution and into said ethylene glycol dinitrate organic phase;
   (b) separating said ethylene glycol dinitrate organic phase from said water solution;
   (c) passing said water solution into a distillation zone and heating said water solution to a temperature of from about 50 degrees F. to about 200 degrees F. at a pressure in the range of from about 10 to about 500 mm of mercury;
   (d) withdrawing a vapor stream from the top of said distillation zone;
   (e) condensing said vapor stream to form a water phase and a nitrated ester phase, said nitrated ester phase consisting essentially of ethylene glycol dinitrate;
   (f) separating said water phase from said nitrated ester phase;
   (g) passing at least a portion of said nitrated ester phase to said extraction zone; and
   (h) withdrawing the bottom product of said distillation zone which comprises water which is substantially free of said nitrated esters.

8. The method of claim 7 wherein said water solution is continuously passed through said extraction zone and to said distillation zone.

9. The method of claim 7 further comprising passing said condensed water phase back to said distillation zone.

10. The method of claim 7 wherein said water solution is continuously passed into the upper section of a packed distillation zone.

11. The method of claim 10 wherein from about 5% to about 80% of the feed water solution is vaporized in said packed distillation zone.

12. The method of claim 7 wherein said nitrated esters further comprise propylene glycol dinitrate.

* * * * *